US010487143B2

(12) United States Patent
Lyerly et al.

(10) Patent No.: US 10,487,143 B2
(45) Date of Patent: Nov. 26, 2019

(54) VACCINES AGAINST HER3 ANTIGENS AND METHODS OF USING THE SAME

(71) Applicant: Duke University, Durham, NC (US)

(72) Inventors: Herbert K. Lyerly, Durham, NC (US); Takuya Osada, Durham, NC (US); Zachary C. Hartman, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/726,177

(22) Filed: Oct. 5, 2017

(65) Prior Publication Data
US 2018/0094050 A1 Apr. 5, 2018

Related U.S. Application Data

(60) Provisional application No. 62/404,538, filed on Oct. 5, 2016.

(51) Int. Cl.
| A61K 39/00 | (2006.01) |
| C07K 16/22 | (2006.01) |
| A61K 39/39 | (2006.01) |
| A61P 35/00 | (2006.01) |
| C12N 15/861 | (2006.01) |
| C12N 15/863 | (2006.01) |
| C07K 14/475 | (2006.01) |
| A61K 47/50 | (2017.01) |
| C07K 14/71 | (2006.01) |
| C07K 14/47 | (2006.01) |
| C12N 15/85 | (2006.01) |

(52) U.S. Cl.
CPC .......... C07K 16/22 (2013.01); A61K 39/0011 (2013.01); A61K 39/39 (2013.01); A61K 47/50 (2017.08); A61P 35/00 (2018.01); C07K 14/475 (2013.01); C07K 14/4748 (2013.01); C07K 14/71 (2013.01); C12N 15/85 (2013.01); C12N 15/863 (2013.01); C12N 15/8613 (2013.01); A61K 2039/505 (2013.01); A61K 2039/53 (2013.01); A61K 2039/57 (2013.01); A61K 2039/572 (2013.01); A61K 2039/585 (2013.01); A61K 2039/6031 (2013.01); C07K 2317/732 (2013.01); C07K 2317/76 (2013.01)

(58) Field of Classification Search
None
See application file for complete search history.

(56) References Cited

U.S. PATENT DOCUMENTS

| 6,734,172 | B2 | 5/2004 | Scholler et al. |
| 8,445,268 | B2 | 5/2013 | Lee et al. |
| 8,846,080 | B2 | 9/2014 | Biemans et al. |
| 9,216,229 | B2 | 12/2015 | Brown et al. |
| 9,226,959 | B2 | 1/2016 | Kramps et al. |
| 9,956,276 | B2 | 5/2018 | Lyerly et al. |
| 2003/0143568 | A1 | 7/2003 | Singer et al. |
| 2003/0228606 | A1 | 12/2003 | Tatarewicz et al. |
| 2003/0232350 | A1 | 12/2003 | Afar et al. |
| 2004/0018971 | A1* | 1/2004 | Fikes ..................... C07K 14/71 424/185.1 |
| 2004/0197314 | A1* | 10/2004 | Delcayre ............... C07K 14/47 424/93.21 |
| 2004/0253606 | A1 | 12/2004 | Aziz et al. |
| 2005/0266409 | A1 | 12/2005 | Brown et al. |
| 2008/0057064 | A1 | 3/2008 | Zhou |
| 2009/0214518 | A1 | 8/2009 | Buckanovich et al. |
| 2010/0055093 | A1 | 3/2010 | Shepard et al. |
| 2010/0279399 | A1 | 11/2010 | Robins et al. |
| 2011/0281748 | A1 | 11/2011 | Singh et al. |
| 2012/0014984 | A1 | 1/2012 | Shahabi |
| 2014/0017259 | A1 | 1/2014 | Aurisicchio et al. |
| 2014/0221329 | A1 | 8/2014 | Cronin et al. |
| 2015/0047065 | A1 | 2/2015 | Covagen |
| 2015/0258099 | A1 | 9/2015 | Hager et al. |

FOREIGN PATENT DOCUMENTS

| WO | 2001/38576 | 5/2001 |
| WO | 2003/080835 | 10/2003 |
| WO | 2011/060260 | 5/2011 |
| WO | 2011/146568 | 11/2011 |
| WO | 2011/154863 | 12/2011 |
| WO | 2012/125864 | 9/2012 |
| WO | 2016/007499 | 1/2016 |
| WO | 2016/007504 | 1/2016 |
| WO | 2017/120576 | 7/2017 |

OTHER PUBLICATIONS

Hartman et al (Vaccine, 2011, 29:9361-9367).*
Mittendorf et al (Annals of Surgical Oncology, 2006, 13:1085-1098).*
Slamon et al (NEJM, 2011, 365:1273-1283).*
Abd El-Rehim, D.M., et al. "Expression and co-expression of the members of the epidermal growth factor receptor (EGFR) family in invasive breast carcinoma." (2004) Br J Cancer 91:1532-42.
Agus, D.B., et al. "Targeting ligand-activiated ErbB2 signaling inhibits breast and prostate tumor growth." (2002) 2:127-37.
Amalfitano, A., et al. "Production and characterization of improved adenovirus vectors with the E1, E2b, and E3 genes deleted" (1998) J Virol. 72(2):926-33.
Alimandi, M., et al. "Cooperative signaling of ErbB3 and ErbB2 in neoplastic transformation and human mammary carcinomas." (1995) Oncogene 10:1813-21.
Amin, D.N., et al. "Resiliency and vulnerability in the HER2-HER3 tumorigenic driver." (2010) Sci Transl Med 2:16-17.
Amin, D.N., et al. "The role of HER3, the unpretentious emmber of the HER family, in cancer biology and cancer therapuetics." (2010) Semin Cell Dev Biol 2010:8.

(Continued)

Primary Examiner — Laura B Goddard
(74) Attorney, Agent, or Firm — Quarles & Brady LLP

(57) ABSTRACT

The invention generally relates to compositions and methods for preventing and treating cancer. More specifically, the invention relates to antigenic polypeptides and their use in cancer vaccines that may be used, in part, to treat cancer types dependent upon HER2-mediated signaling.

19 Claims, 2 Drawing Sheets
Specification includes a Sequence Listing.

(56) References Cited

OTHER PUBLICATIONS

Arpino, G., et al. "Crosstalk between the estrogen receptor and the HER tyrosine kinase receptor family: molecular mechanism and clinical implications for endocrine therapy resistance" (2008) Endocr Rev.29(2):217-33.

Arteaga, C. et al. "Treatment of HER2-positive breast cancer: current status and future perspectives" (2012) Nature Reviews Clinical Oncology, 9: 16-32.

Atkins, M.B., et al. "Phase I evaluation of intravenous recombinant human interleukin 12 in patients with advanced malignancies." (1997) Clin Cancer Res 3:409-17.

Bae, S.Y., et al. "HER3 status by immunohistochemistry is correlated with poor prognosis in hormone receptor-negative breast cancer patients" (2013) Breast Cancer Res Treat. 139(3):741-50.

Begnami, M.D., et al. "Prognostic implications of altered human epidermal growth factor receptors (HERs) in gastric carcinomas: HER2 and HER3 are predictors of poor outcome" (2011) J Clin Oncol. 29(22):3030-6.

Ben-Kasus, T. et al. "Persistent elimination of ErbB-2/HER2-overexpressing tumors using combinations of monoclonal antibodies: relevance of receptor endocytosis." (2009) Proc Natl Acad Sci USA 106:3294-99.

Binder, D.C., et al. "Antigen-specific bacterial vaccine combined with anti-PD-L1 rescues dysfunctional endogenous T cells to reject long-established cancer" (2013) Cancer immunology research 1(2):123-33.

Blattman, J.N., et al. "Cancer immunotherapy: a treatment for the masses." (2004) Science 305:200-5.

Cai., Z., et al. "Targeting erbB receptors" 2010 Seminars in cell & developmental biology 21(9):961-6.

Campbell, M.R., et al. "HER3 comes of age: new insights into its functions and role in signaling, tumor biology, and cancer therapy." Clin cancer Res (2010) 16:1373-83.

Chiu, C.G., et al. "HER-3 overexpression is prognostic of reduced breast cancer survival: a study of 4046 patients" (2010) Annals of surgery 251(6):1107-16.

Clay, T. et al., "Polyclonal Immune Responses to Antigens Associated With Cancer Signaling Pathways and New Strategies to Enhance Cancer Vaccines" (2011) Immunolo Res 49(0): 235-247.

Desbois-Mouthon, C., et al. "Insulin-like growth factor-1 receptor inhibition induces a resistance mechanism via the epidermal growth factor receptor/HER3/AKT signaling pathway: rational basis for cotargeting insulin-line growth factor-1 receptor and epidermal growth factor receptor in hepatocellular carcinoma." (2009) Clin Cancer Res 15:5445-56.

Drake, C.G., et al. Mechanisms of immune evasion by tumors. (2006) Adv Immunol 90:51-81.

Dranoff, G. "Cytokines in cancer pathogenesis and cancer therapy." (2004) Nat Rev Cancer 4:11-22.

Eager, R., et al. "GM-CSFF gene-transduced tumor vaccines." (2005) Mol Ther. 12:18-27.

Emens, L.A., et al. "Abstract PD1-6: Inhibition of PD-L1 by MPDL3280A leads to clinical activity in patients with metastatic triple-negative breast cancer" (2015) Cancer Res. 75(9 Supplement):PD1-6-PD1-6.

Erjala, K., et al. "Signaling via ErbB2 and ErbB3 associates with resistance and epidermal growth factor receptor (EGFR) amplication with sensitivity to EGFR inhibitor gefitnib in head and neck squamous cell carcinoma cells." (2006) Clin Cancer Res 12:4103-11.

Folgiero, V., et al. "Induction of ErbB-3 expression by alpha6beta4 integrin contributes to tamoxifen resistance in ERbetal-negative breast carcinomas" (2008) PLoS One 3(2):e1592.

Fourcade, J., et al. "PD-1 and Tim-3 regulate the expansion of tumor antigen-specific CD8(+) T cells induced by melanoma vaccines" (2014) Cancer Res. 74(4):1045-55.

Frogne, T., et al. "Activation of ErbB3, EGFR and Erk is essential for growth of human breast cancer cell lines with acquired resistance to fulvestrant." (2009) Breast Cancer Res Treat 114:263-75.

Friedman, L.M., et al. "Synergistic down-regulation of receptor tyrosine kinase by combinations of mAbs: implications for cancer immunotherapy." (2005) Proc Natl Acad Sci USA 102:1915-20.

Fu, J. et al., "Preclinical evidence that PD1 blockade cooperates with cancer vaccine TEGVAX to elicit regression of established tumors" (2014) Cancer Res, 74(15): 4042-4052.

Gala, K., & Chandarlapaty, S. "Molecular pathways: HER3 targeted therapy" (2014) Clin Cancer Res 20(6):1410-6.

Gallo, P. et al., "Xenogenic Immunization in Mice Using HER2 DNA Delivered by an Adenoviral Vector" (2005) Int. J. Cancer 113(1): 67-77.

Giltnane, J.M., et al. "Quantitative multiplexed analysis of ErbB family coexpression for primary breast cancer prognosis in a large retrospective cohor" (2009) Cancer 115(11):2400-9.

Goldman, B., et al. "The cancer vaccine roller coaster." (2009) Nat Biotechnol 27:129-39.

Greenspan, N.S., et al. "Defining epitopes: It's not as easy as it seems," (1999) Nature Biotechnology 7:936-937.

Grupp, S., et al. Chimeric antigen receptor-modified T cells for acute lymphoid leukemia. New England J. Med. 368:1509-18, (2013).

Hartman, Z., et al. "An Adenoviral vaccine encoding full-length inactivated human Her2 exhibits potent immunogenicity and enhanced therapeutic efficacy without oncogenicity" (2010) Clin Cancer Res 16(5): 1466-1477.

Hartman, Z., et al. "Ligand-independent TLR signals generated by ectopic overexpression of MyD88 generate local and systemic anti-tumor immunity" (2010) Cancer Res 70(18): 7209-7220.

Hartman, Z., et al. "Growth of triple-negative breast cancer cells relies upon coordinate autocrine expression of the proinflammatory cytokines IL-6 and IL-8" (2013) Cancer Res 73(11): 3470-3480.

Hartman, Z., et al. "Increasing vaccine potency through exosome antigen targeting" (2011) Vaccine Nov. 21;29(50):9361-7.

Hayashi, M., et al. "High expression of HER3 is associated with a decreased survival in gastric cancer" (2008) Clin Cancer Res 14(23):7843-9.

He, T.C., et al. "A simplified system for generating recombinant adenoviruses." (1998) Proc Natl Acad Sci USA 95:2509-14.

Holbro, T., et al. "The ErbB2/ErbB3 heterodimer functions as an oncogenic unti: ErbB2 requires ErbB3 to drive breast tumer cell proliferation." (2003) Proc Natl Acad Sci USA 100:8933-8.

Hsieh, A.C. & Moasser, M.M. "Targeting HER proteins in cancer therapy and the role of the non-target HER3" (2007) Br J Cancer. 97(4):453-7.

Huang, X. et al. "Heterotrimerization of the growth factor receptors erbB2, erbB3, and insulin-like growth facotr-I receptor in breast cancer cells resistant to perception." (2010) Cancer Res 70:1204-14.

Ignatiadis, M. & Sotiriou, C. "Luminal breast cancer: from biology to treatment" (2013) Nature Rev Clin Oncol 10, 494-506.

Junttila, T.T., et al. "Ligand-independent HER2/HER3/PI3K complex is disrupted by trastuzumab and is effectively inhibited by the PI3K inhibitor GDC-0941" 2009 Cancer Cell 15(5):429-40.

Kanzler, H., et al. "Therapeutic targeting of innate immunity with Toll-like receptor agonists and antagonists." (2007) Nat Med 13:552-9.

Karyampudi, L., et al. "Accumulation of memory precursor CD8 T cells in regressing tumors following combination therapy with vaccine and anti-PD-1 antibody" 2014 Cancer Res 74(11):2974-85.

Kershaw, M.H. et al., "Gene-engineered T cells as a superior adjuvant therapy for metastatic cancer" (2004) J Immunol 173(3): 2143-2150.

Kol, A., et al. "HER3, serious partner in crime: therapeutic approaches and potential biomarkers for effect of HER3-targeting". Pharmacol Ther. 2014;143(1):1-11.

Laheru, D.A., et al. "Genes to vaccines for immunotherapy: how the molecular biology revolution has influenced cancer immunology." (2005) Mol Cancer Ther 4:1645-52.

Lee, C.H., et al. "Assessment of Her-1, Her-2, and Her-3 expression and Her-2 amplification in advanced stage ovarian carcinoma". Int J Gynecol Pathol. 2005;24(2):147-52.

(56) References Cited

OTHER PUBLICATIONS

Lee-Hoeflich, S.T., et al. "A central role for HER3 in HER2-amplified breast cancer: implications for targeted therapy." (2008) Cancer Res 68:5878-87.
Leonard, J.P., et al. "Effects of single-dose interleukin-12 exposure on interleukin-12-associated toxicity and interferon-y production." (1997) Blood 90:2541-8.
Li, B., et al. "Anti-programmed death-1 synergizes with granulocyte macrophage colony-stimulating factor—secreting tumor cell immunotherapy providing therapeutic benefit to mice with established tumors". Clin Cancer Res. 2009;15(5):1623-34.
Liddy, N., et al., Monoclonal TCR-redirected tumor cell killing Nature Med. 18:980-7 (2012).
Liu, B., et al. Downregulation of erbB3 abrogates erbB2-mediated tamoxifen resistance in breast cancer cells. (2007) Int J Cancer 120:1874-82.
Luo, J., et al. "A protocol for rapid generation of recombinant adenoviruses using the AdEasy system" (2007) Nature Protocols 2:1236.
Makhija, S., et al. "Clinical activity of gemcitabine plus pertuzumab in platinum-resistant ovarian cancer, fallopian tube cancer, or primary peritoneal cancer." (2010) J Clin Oncol 28:1215-23.
Miller, T.W., et al. "Loss of Phosphatase and Tensin homologue deleted on chromosome 10 enages ErbB3 and insulin-like growth factor-I receptor signaling to promote antiestrogen resistance in breast cancer." (2009) Cancer Res 69:4192-201.
Morse, M.A., et al. Synergism from combined immunologic and pharmacologic inhibition of HER2 in vivo. (2010) Int J Cancer 126:2893-903.
Musgrove, E.A. & Sutherland, R.L. Biological determinants of endocrine resistance in breast cancer. Nat Rev Cancer. 2009;9(9):631-43.
Nabholtz, J.M., et al., "Anastrozole is superior to tamoxifen as first-line therapy for advanced breast cancer in postmenopausal women: results of a North American multicenter randomized trial. Arimidex Study Group" (2000) J Clin Oncol 18(22): 3758-3767.
Nanda, R., et al. Pembrolizumab in Patients With Advanced Triple-Negative Breast Cancer: Phase Ib Keynote-012 Study. J Clin Oncol. 2016;34(21):2460-7.
Nitta, T., et al., "Preliminary trial of specific targeting therapy against malignant glioma" Lancet 355:368-371 (1990).
Norton, J.A., et al. "Inhibition of host signal transducer and activator of transcription factor 6 results in cure with cyclophosphamide and interleukin 12 immunotherapy." (2006) Ann Surg Oncol 13:118-24.
O'Neil, L.A., et al. "Therapeutic targeting of toll-like receptors for infectious and inflammatory diseases and cancer." (2009) Pharmacol Rev 61:177-97.
Osada, T., et al. "Vaccination targeting human HER3 alters the phenotype of infiltrating T cells and responses to immune checkpoint inhibition." (2017). OncoImmunology 0(0).
Osipo, C., et al. "Role for HER2/neu and HER3 in fulvestrant-resistant breast cancer." (2007) Int J Oncol 30:509-20.
Pederson, M.W., et al. "Sym004: a novel synergistic anti-epidermal growth factor receptor antibody mixture with superior anticancer efficacy." (2010) Cancer Res 70:588-97.
Prigent, S.A., et al. "Identification of c-erbB-3 binding sites for phosphatidylinositol 3'-kinase and SHC using an EGF receptor/c-erbB-3 chimera." (1994) Embo J 13:2831-41.
Pulaski, B.A., et al. "Reduction of established spontaneous mammary carcinoma metastases following immunotherapy with major histocompatibility complex class II and B7.1 cell-based tumor vaccines." (1998) Cancer Res. 58:1486-93.
Renard, V. et al., "HER-2 DNA and Protein Vaccines Containing Potent Th Cell Epitopes Induce Distinct Protective and Therapeutic Antitumor Responses in HER-2 Transgenic Mice" (2003) J Immunol 171(3): 1588-1595.
Ren, X.R., et al. "Polyclonal Her2-specific antibodies induced by vaccination mediate receptor internalization and degradation in tumor cells" (2012) Breast cancer research 14: R89.

Reschke, M., et al. "HER3 is a determinant for poor prognosis in melanoma". Clin Cancer Res. 2008;14(16):5188-97.
Rosenberg, S.A., et al. "Adoptive cell transfer: a clinical path to effective cancer immunotherapy" Nat. Rev. Cancer 8 (4): 299-308 (2008).
Roskoski, R. Jr. "The ErbB/HER family of protein-tyrosine kinases and cancer". Pharmacological research : the official journal of the Italian Pharmacological Society. 2014;79:34-74.
Sakai, K., et al. "A novel HER dimerization inhibitor, inhibits the growth of human lung cancer cells mediated by the HER3 signaling pathway". Cancer Sci. 2007;98(9):1498-503.
Schoeberl, B., et al. "An ErbB3 Antibody, MM-121, Is Active in Cancers with Ligand-Dependent Activation" (2010) Cancer Research: 70(6): 2485-2494.
Sergina, N.V., et al. "Escape from HER-family tyrosine kinase inhibitor therapy by the kinase-inactive HER3." (2007) Nature 445:437-41.
Shin, D.S. & Ribas, A. "The evolution of checkpoint blockade as a cancer therapy: what's here, what's next?" Curr Opin Immunol. 2015;33:23-35.
Soares, K.C., et al. "PD-1/PD-L1 blockade together with vaccine therapy facilitates effector T-cell infiltration into pancreatic tumors". J Immunother. 2015;38(1):1-11.
Soltoff, S.P., et al. "ErbB3 is involved in activation of phosphatidylinositol 3-kinase by epidermal growth factor." (1994) Mol Cell Biol 14:3550-3558.
Takikita, M., et al. "Membranous expression of Her3 is associated with a decreased survival in head and neck squamous cell carcinoma". J Transl Med. 2011;9:126.
Tanaka, T. et al., "Efficient generation of antibodies to oncoproteins by using synthetic peptide antigens," (1985) Proc. Natl. Acad. Sci. USA 82:3400-3404.
Tiriveedhi, V., et al. "Safety and preliminary evidence of biologic efficacy of a mammaglobin-a DNA vaccine in patients with stable metastatic breast cancer". Clinical cancer research : an official journal of the American Association for Cancer Research. 2014;20(23):5964-75.
Topalian, S.L., et al. "Immune checkpoint blockade: a common denominator approach to cancer therapy". Cancer Cell. 2015;27(4):450-61.
Tovey, S., et al. "Can molecular markers predict when to implement treatment with aromatase inhibitors in invasive breast cancer?" Clin Cancer Res. 2005;11(13):4835-42.
Van Elsas, A., et al. "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation". J Exp Med. 1999;190(3):355-66.
Wong, R.M., et al. "Programmed death-1 blockade enhances expansion and functional capacity of human melanoma antigen-specific CTLs". International immunology. 2007;19(10):1223-34.
Xia, W., et al. "An heregulin-EGFR-HER3 autocrine signaling axis can mediate acquired lapatinib resistance in HER2+ breast cancer models" (2013) Breast cancer research 15(5):R85.
Yoo, J.Y., et al., "Downregulation of ErbB3 Expression by Adenovirus Expressing ErbB3 Specific shRNA Enhances Antitumor Efficacy through Apoptosis Induction" (2009) Molecular Therapy: 17(Suppl. 1): S106.
Yuan, J., et al., "CTLA-4 blockade increases antigen-specific CD8(+) T cells in prevaccinated patients with melanoma: three cases" (2011) Cancer Immunol Immunother, 60(8): 1137-1146.
Yu, P., et al. "Targeting the primary tumor to generate CTL for the effective eradication of spontaneous metastases." (2007) J Immunol 179:1960-8.
Zhang, Y., et al. "EBP1, an ErbB3-binding protein, is decreased in prostate cancer and implicated in hormone resistance." (2008) Mol Cnacer Ther 7:3176-86.
Zitvogel, L., et al. "The anticancer immune response: indispensable for therapeutic success?" (2008) 118:1991-2001.

\* cited by examiner

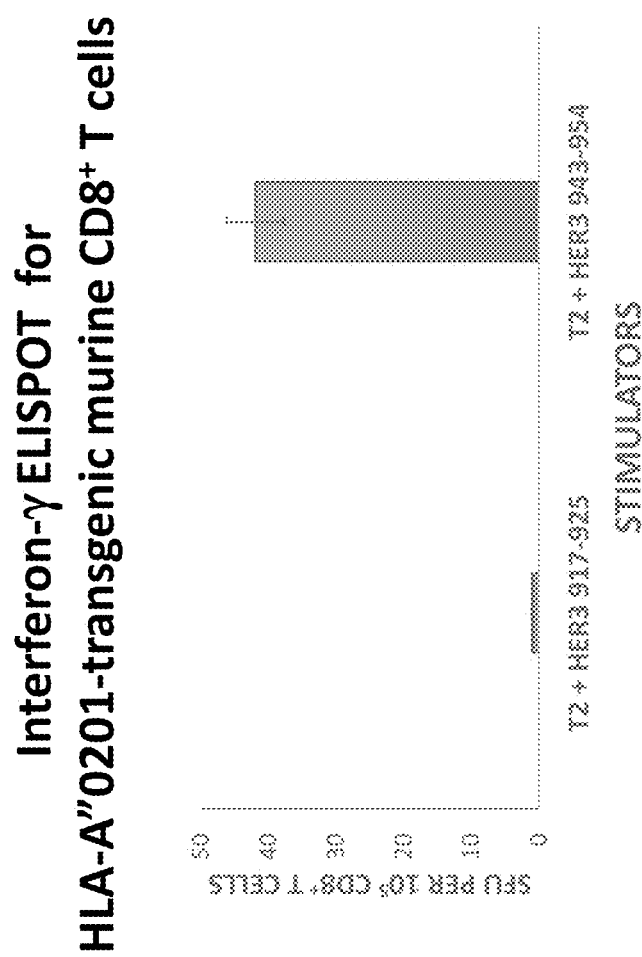

SEQUENCE LISTING

<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: Synthetic: HER3 Antigen 1

<400> SEQUENCE: 1

Leu Ala Glu Val Pro Asp Leu Leu Glu
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic: HER3 Antigen 2

<400> SEQUENCE: 2

Tyr Met Val Met Val Lys Cys Trp Met Ile Asp Glu Asn Ile
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic: HER3 Antigen 3

<400> SEQUENCE: 3

Val Met Val Lys Cys Trp Met Ile Asp Glu Asn Ile
1               5                   10

<210> SEQ ID NO 4
<211> LENGTH: 351
<212> TYPE: PRT
<213> ORGANISM: Artificial Sequence
<220> FEATURE:
<223> OTHER INFORMATION: Synthetic: C1C2 domains of mouse lactadherin

<400> SEQUENCE: 4

Thr Glu Tyr Ile Cys Gln Cys Pro Val Gly Tyr Ser Gly Ile His Cys
1               5                   10                  15

Glu Thr Gly Cys Ser Thr Gln Leu Gly Met Glu Gly Gly Ala Ile Ala
            20                  25                  30

Asp Ser Gln Ile Ser Ala Ser Ser Val Tyr Met Gly Phe Met Gly Leu
        35                  40                  45

Gln Arg Trp Gly Pro Glu Leu Ala Arg Leu Tyr Arg Thr Gly Ile Val
    50                  55                  60

Asn Ala Trp Thr Ala Ser Asn Tyr Asp Ser Lys Pro Trp Ile Gln Val
65                  70                  75                  80

Asn Leu Leu Arg Lys Met Arg Val Ser Gly Val Met Thr Gln Gly Ala
                85                  90                  95

Ser Arg Ala Gly Arg Ala Glu Tyr Leu Lys Thr Phe Lys Val Ala Tyr
            100                 105                 110

Ser Leu Asp Gly Arg Lys Phe Glu Phe Ile Gln Asp Glu Ser Gly Gly
        115                 120                 125

Asp Lys Glu Phe Leu Gly Asn Leu Asp Asn Asn Ser Leu Lys Val Asn
    130                 135                 140

Met Phe Asn Pro Thr Leu Glu Ala Gln Tyr Ile Lys Leu Tyr Pro Val

-continued

```
                145                 150                 155                 160
        Ser Cys His Arg Gly Cys Thr Leu Arg Phe Glu Leu Leu Gly Cys Glu
                        165                 170                 175

Leu His Gly Cys Ser Glu Pro Leu Gly Leu Lys Asn Asn Thr Ile Pro
                        180                 185                 190

Asp Ser Gln Met Ser Ala Ser Ser Tyr Lys Thr Trp Asn Leu Arg
                    195                 200                 205

Ala Phe Gly Trp Tyr Pro His Leu Gly Arg Leu Asp Asn Gln Gly Lys
                        210                 215                 220

Ile Asn Ala Trp Thr Ala Gln Ser Asn Ser Ala Lys Glu Trp Leu Gln
        225                 230                 235                 240

Val Asp Leu Gly Thr Gln Arg Gln Val Thr Gly Ile Ile Thr Gln Gly
                        245                 250                 255

Ala Arg Asp Phe Gly His Ile Gln Tyr Val Ala Ser Tyr Lys Val Ala
                        260                 265                 270

His Ser Asp Asp Gly Val Gln Trp Thr Val Tyr Glu Glu Gln Gly Ser
                        275                 280                 285

Ser Lys Val Phe Gln Gly Asn Leu Asp Asn Asn Ser His Lys Lys Asn
                    290                 295                 300

Ile Phe Glu Lys Pro Phe Met Ala Arg Tyr Val Arg Val Leu Pro Val
        305                 310                 315                 320

Ser Trp His Asn Arg Ile Thr Leu Arg Leu Glu Leu Leu Gly Cys Phe
                        325                 330                 335

Glu Gln Lys Leu Ile Ser Glu Glu Asp Leu Asn Met His Thr Gly
                    340                 345                 350
```

```
<210> SEQ ID NO 5
<211> LENGTH: 24
<212> TYPE: PRT
<213> ORGANISM: Artificial Sequence
<220> FEATURE:
<223> OTHER INFORMATION: Synthetic: leader sequence of mouse lactadherin

<400> SEQUENCE: 5

Met Gln Val Ser Arg Val Leu Ala Ala Leu Cys Gly Met Leu Leu Cys
1               5                   10                  15

Ala Ser Gly Leu Phe Ala Ala Ser
            20

<210> SEQ ID NO 6
<211> LENGTH: 327
<212> TYPE: PRT
<213> ORGANISM: Artificial Sequence
<220> FEATURE:
<223> OTHER INFORMATION: Synthetic: C1C2 domains of human lactadherin

<400> SEQUENCE: 6

Tyr Ala Gly Asn His Cys Glu Thr Lys Cys Val Glu Pro Leu Gly Met
1               5                   10                  15

Glu Asn Gly Asn Ile Ala Asn Ser Gln Ile Ala Ala Ser Ser Val Arg
                20                  25                  30

Val Thr Phe Leu Gly Leu Gln His Trp Val Pro Glu Leu Ala Arg Leu
            35                  40                  45

Asn Arg Ala Gly Met Val Asn Ala Trp Thr Pro Ser Ser Asn Asp Asp
        50                  55                  60

Asn Pro Trp Ile Gln Val Asn Leu Leu Arg Arg Met Trp Val Thr Gly
65                  70                  75                  80
```

```
Val Val Thr Gln Gly Ala Ser Arg Leu Ala Ser His Glu Tyr Leu Lys
            85                  90                  95

Ala Phe Lys Val Ala Tyr Ser Leu Asn Gly His Glu Phe Asp Phe Ile
            100                 105                 110

His Asp Val Asn Lys Lys His Lys Glu Phe Val Gly Asn Trp Asn Lys
            115                 120                 125

Asn Ala Val His Val Asn Leu Phe Glu Thr Pro Val Glu Ala Gln Tyr
            130                 135                 140

Val Arg Leu Tyr Pro Thr Ser Cys His Thr Ala Cys Thr Leu Arg Phe
145                 150                 155                 160

Glu Leu Leu Gly Cys Glu Leu Asn Gly Cys Ala Asn Pro Leu Gly Leu
                165                 170                 175

Lys Asn Asn Ser Ile Pro Asp Lys Gln Ile Thr Ala Ser Ser Ser Tyr
            180                 185                 190

Lys Thr Trp Gly Leu His Leu Phe Ser Trp Asn Pro Ser Tyr Ala Arg
            195                 200                 205

Leu Asp Lys Gln Gly Asn Phe Asn Ala Trp Val Ala Gly Ser Tyr Gly
            210                 215                 220

Asn Asp Gln Trp Leu Gln Val Asp Leu Gly Ser Ser Lys Glu Val Thr
225                 230                 235                 240

Gly Ile Ile Thr Gln Gly Ala Arg Asn Phe Gly Ser Val Gln Phe Val
                245                 250                 255

Ala Ser Tyr Lys Val Ala Tyr Ser Asn Asp Ser Ala Asn Trp Thr Glu
            260                 265                 270

Tyr Gln Asp Pro Arg Thr Gly Ser Ser Lys Ile Phe Pro Gly Asn Trp
            275                 280                 285

Asp Asn His Ser His Lys Lys Asn Leu Phe Glu Thr Pro Ile Leu Ala
            290                 295                 300

Arg Tyr Val Arg Ile Leu Pro Val Ala Trp His Asn Arg Ile Ala Leu
305                 310                 315                 320

Arg Leu Glu Leu Leu Gly Cys
                325

<210> SEQ ID NO 7
<211> LENGTH: 8
<212> TYPE: PRT
<213> ORGANISM: Artificial Sequence
<220> FEATURE:
<223> OTHER INFORMATION: Synthetic: leader sequence of human lactadherin

<400> SEQUENCE: 7

Tyr Thr Cys Thr Cys Leu Lys Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic: HER3 antigen 4

<400> SEQUENCE: 8

Ile Lys Val Ile Glu Asp Lys Ser Gly
1               5

<210> SEQ ID NO 9
<211> LENGTH: 1342
<212> TYPE: PRT
<213> ORGANISM: Homo sapiens
```

<220> FEATURE:
<221> NAME/KEY: misc_feature
<223> OTHER INFORMATION: Human HER3 Protein Precursor amino acid sequence

<400> SEQUENCE: 9

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
370                 375                 380
```

```
Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
        420                 425                 430

Met Lys Asn Leu Asn Val Thr Ser Leu Gly Phe Arg Ser Leu Lys Glu
    435                 440                 445

Ile Ser Ala Gly Arg Ile Tyr Ile Ser Ala Asn Arg Gln Leu Cys Tyr
450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
        500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
        580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
            645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
            725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
        770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
```

```
                    805                 810                 815
Gln Ile Ala Lys Gly Met Tyr Tyr Leu Glu Glu His Gly Met Val His
                820                 825                 830
Arg Asn Leu Ala Ala Arg Asn Val Leu Leu Lys Ser Pro Ser Gln Val
                835                 840                 845
Gln Val Ala Asp Phe Gly Val Ala Asp Leu Leu Pro Pro Asp Asp Lys
                850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                885                 890                 895
Tyr Gly Val Thr Val Trp Glu Leu Met Thr Phe Gly Ala Glu Pro Tyr
                900                 905                 910
Ala Gly Leu Arg Leu Ala Glu Val Pro Asp Leu Leu Glu Lys Gly Glu
                915                 920                 925
Arg Leu Ala Gln Pro Gln Ile Cys Thr Ile Asp Val Tyr Met Val Met
                930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                965                 970                 975
Val Ile Lys Arg Glu Ser Gly Pro Gly Ile Ala Gly Pro Glu Pro
                980                 985                 990
His Gly Leu Thr Asn Lys Lys Leu  Glu Glu Val Glu Leu  Glu Pro Glu
                995                 1000                1005
Leu Asp  Leu Asp Leu Asp Leu  Glu Ala Glu Glu Asp  Asn Leu Ala
1010                 1015                1020
Thr Thr  Thr Leu Gly Ser Ala  Leu Ser Leu Pro Val  Gly Thr Leu
1025                 1030                1035
Asn Arg  Pro Arg Gly Ser Gln  Ser Leu Leu Ser Pro  Ser Ser Gly
1040                 1045                1050
Tyr Met  Pro Met Asn Gln Gly  Asn Leu Gly Gly Ser  Cys Gln Glu
1055                 1060                1065
Ser Ala  Val Ser Gly Ser Ser  Glu Arg Cys Pro Arg  Pro Val Ser
1070                 1075                1080
Leu His  Pro Met Pro Arg Gly  Cys Leu Ala Ser Glu  Ser Ser Glu
1085                 1090                1095
Gly His  Val Thr Gly Ser Glu  Ala Glu Leu Gln Glu  Lys Val Ser
1100                 1105                1110
Met Cys  Arg Ser Arg Ser Arg  Ser Arg Ser Pro Arg  Pro Arg Gly
1115                 1120                1125
Asp Ser  Ala Tyr His Ser Gln  Arg His Ser Leu Leu  Thr Pro Val
1130                 1135                1140
Thr Pro  Leu Ser Pro Pro Gly  Leu Glu Glu Glu Asp  Val Asn Gly
1145                 1150                1155
Tyr Val  Met Pro Asp Thr His  Leu Lys Gly Thr Pro  Ser Ser Arg
1160                 1165                1170
Glu Gly  Thr Leu Ser Ser Val  Gly Leu Ser Ser Val  Leu Gly Thr
1175                 1180                1185
Glu Glu  Glu Asp Glu Asp Glu  Glu Tyr Glu Tyr Met  Asn Arg Arg
1190                 1195                1200
Arg Arg  His Ser Pro Pro His  Pro Pro Arg Pro Ser  Ser Leu Glu
1205                 1210                1215
```

```
Glu Leu Gly Tyr Glu Tyr Met Asp Val Gly Ser Asp Leu Ser Ala
    1220                1225                1230

Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 10
<211> LENGTH: 678
<212> TYPE: PRT
<213> ORGANISM: Homo sapiens
<220> FEATURE:
<221> NAME/KEY: misc_feature
<223> OTHER INFORMATION: Intracellular domain of HER3  665-1342

<400> SEQUENCE: 10

Tyr Trp Arg Gly Arg Arg Ile Gln Asn Lys Arg Ala Met Arg Tyr
1               5                   10                  15

Leu Glu Arg Gly Glu Ser Ile Glu Pro Leu Asp Pro Ser Glu Lys Ala
                    20                  25                  30

Asn Lys Val Leu Ala Arg Ile Phe Lys Glu Thr Glu Leu Arg Lys Leu
            35                  40                  45

Lys Val Leu Gly Ser Gly Val Phe Gly Thr Val His Lys Gly Val Trp
50                  55                  60

Ile Pro Glu Gly Glu Ser Ile Lys Ile Pro Val Cys Ile Lys Val Ile
65                  70                  75                  80

Glu Asp Lys Ser Gly Arg Gln Ser Phe Gln Ala Val Thr Asp His Met
                85                  90                  95

Leu Ala Ile Gly Ser Leu Asp His Ala His Ile Val Arg Leu Leu Gly
            100                 105                 110

Leu Cys Pro Gly Ser Ser Leu Gln Leu Val Thr Gln Tyr Leu Pro Leu
        115                 120                 125

Gly Ser Leu Leu Asp His Val Arg Gln His Arg Gly Ala Leu Gly Pro
    130                 135                 140

Gln Leu Leu Leu Asn Trp Gly Val Gln Ile Ala Lys Gly Met Tyr Tyr
145                 150                 155                 160

Leu Glu Glu His Gly Met Val His Arg Asn Leu Ala Ala Arg Asn Val
                165                 170                 175

Leu Leu Lys Ser Pro Ser Gln Val Gln Val Ala Asp Phe Gly Val Ala
            180                 185                 190

Asp Leu Leu Pro Pro Asp Asp Lys Gln Leu Leu Tyr Ser Glu Ala Lys
        195                 200                 205

Thr Pro Ile Lys Trp Met Ala Leu Glu Ser Ile His Phe Gly Lys Tyr
```

```
                210                 215                 220
Thr His Gln Ser Asp Val Trp Ser Tyr Gly Val Thr Val Trp Glu Leu
225                 230                 235                 240

Met Thr Phe Gly Ala Glu Pro Tyr Ala Gly Leu Arg Leu Ala Glu Val
                    245                 250                 255

Pro Asp Leu Leu Glu Lys Gly Glu Arg Leu Ala Gln Pro Gln Ile Cys
                260                 265                 270

Thr Ile Asp Val Tyr Met Val Met Val Lys Cys Trp Met Ile Asp Glu
            275                 280                 285

Asn Ile Arg Pro Thr Phe Lys Glu Leu Ala Asn Glu Phe Thr Arg Met
290                 295                 300

Ala Arg Asp Pro Pro Arg Tyr Leu Val Ile Lys Arg Glu Ser Gly Pro
305                 310                 315                 320

Gly Ile Ala Pro Gly Pro Glu Pro His Gly Leu Thr Asn Lys Lys Leu
                    325                 330                 335

Glu Glu Val Glu Leu Glu Pro Glu Leu Asp Leu Asp Leu Asp Leu Glu
                340                 345                 350

Ala Glu Glu Asp Asn Leu Ala Thr Thr Thr Leu Gly Ser Ala Leu Ser
            355                 360                 365

Leu Pro Val Gly Thr Leu Asn Arg Pro Arg Gly Ser Gln Ser Leu Leu
370                 375                 380

Ser Pro Ser Ser Gly Tyr Met Pro Met Asn Gln Gly Asn Leu Gly Gly
385                 390                 395                 400

Ser Cys Gln Glu Ser Ala Val Ser Gly Ser Ser Glu Arg Cys Pro Arg
                    405                 410                 415

Pro Val Ser Leu His Pro Met Pro Arg Gly Cys Leu Ala Ser Glu Ser
                420                 425                 430

Ser Glu Gly His Val Thr Gly Ser Glu Ala Glu Leu Gln Glu Lys Val
            435                 440                 445

Ser Met Cys Arg Ser Arg Ser Arg Ser Arg Ser Pro Arg Pro Arg Gly
450                 455                 460

Asp Ser Ala Tyr His Ser Gln Arg His Ser Leu Leu Thr Pro Val Thr
465                 470                 475                 480

Pro Leu Ser Pro Pro Gly Leu Glu Glu Glu Asp Val Asn Gly Tyr Val
                    485                 490                 495

Met Pro Asp Thr His Leu Lys Gly Thr Pro Ser Ser Arg Glu Gly Thr
                500                 505                 510

Leu Ser Ser Val Gly Leu Ser Ser Val Leu Gly Thr Glu Glu Glu Asp
            515                 520                 525

Glu Asp Glu Glu Tyr Glu Tyr Met Asn Arg Arg Arg Arg His Ser Pro
530                 535                 540

Pro His Pro Pro Arg Pro Ser Ser Leu Glu Glu Leu Gly Tyr Glu Tyr
545                 550                 555                 560

Met Asp Val Gly Ser Asp Leu Ser Ala Ser Leu Gly Ser Thr Gln Ser
                    565                 570                 575

Cys Pro Leu His Pro Val Pro Ile Met Pro Thr Ala Gly Thr Thr Pro
                580                 585                 590

Asp Glu Asp Tyr Glu Tyr Met Asn Arg Gln Arg Asp Gly Gly Gly Pro
            595                 600                 605

Gly Gly Asp Tyr Ala Ala Met Gly Ala Cys Pro Ala Ser Glu Gln Gly
610                 615                 620

Tyr Glu Glu Met Arg Ala Phe Gln Gly Pro Gly His Gln Ala Pro His
625                 630                 635                 640
```

```
Val His Tyr Ala Arg Leu Lys Thr Leu Arg Ser Leu Glu Ala Thr Asp
                645                 650                 655

Ser Ala Phe Asp Asn Pro Asp Tyr Trp His Ser Arg Leu Phe Pro Lys
            660                 665                 670

Ala Asn Ala Gln Arg Thr
        675

<210> SEQ ID NO 11
<211> LENGTH: 214
<212> TYPE: PRT
<213> ORGANISM: Homo sapiens
<220> FEATURE:
<221> NAME/KEY: misc_feature
<223> OTHER INFORMATION: HER3 741-954

<400> SEQUENCE: 11

Ile Lys Val Ile Glu Asp Lys Ser Gly Arg Gln Ser Phe Gln Ala Val
1               5                   10                  15

Thr Asp His Met Leu Ala Ile Gly Ser Leu Asp His Ala His Ile Val
                20                  25                  30

Arg Leu Leu Gly Leu Cys Pro Gly Ser Ser Leu Gln Leu Val Thr Gln
            35                  40                  45

Tyr Leu Pro Leu Gly Ser Leu Leu Asp His Val Arg Gln His Arg Gly
        50                  55                  60

Ala Leu Gly Pro Gln Leu Leu Leu Asn Trp Gly Val Gln Ile Ala Lys
65                  70                  75                  80

Gly Met Tyr Tyr Leu Glu Glu His Gly Met Val His Arg Asn Leu Ala
                85                  90                  95

Ala Arg Asn Val Leu Leu Lys Ser Pro Ser Gln Val Gln Val Ala Asp
                100                 105                 110

Phe Gly Val Ala Asp Leu Leu Pro Pro Asp Asp Lys Gln Leu Leu Tyr
            115                 120                 125

Ser Glu Ala Lys Thr Pro Ile Lys Trp Met Ala Leu Glu Ser Ile His
        130                 135                 140

Phe Gly Lys Tyr Thr His Gln Ser Asp Val Trp Ser Tyr Gly Val Thr
145                 150                 155                 160

Val Trp Glu Leu Met Thr Phe Gly Ala Glu Pro Tyr Ala Gly Leu Arg
                165                 170                 175

Leu Ala Glu Val Pro Asp Leu Leu Glu Lys Gly Glu Arg Leu Ala Gln
                180                 185                 190

Pro Gln Ile Cys Thr Ile Asp Val Tyr Met Val Met Val Lys Cys Trp
            195                 200                 205

Met Ile Asp Glu Asn Ile
        210
```

VACCINES AGAINST HER3 ANTIGENS AND METHODS OF USING THE SAME

CROSS-REFERENCE TO RELATED APPLICATIONS

This application claims the benefit of priority of U.S. Provisional Patent Application No. 62/404,538, filed Oct. 5, 2016, which is incorporated herein by reference in its entirety.

STATEMENT REGARDING FEDERALLY SPONSORED RESEARCH

This invention was made with United States government support awarded by the U.S. Department of Defense grant number W81XWH-12-1-057. The United States has certain rights in this invention.

SEQUENCE LISTING

This application is being filed electronically via EFS-Web and includes an electronically submitted Sequence Listing in .txt format. The .txt file contains a sequence listing entitled "2017-10-05 5667-00415_ST25.txt" created on Oct. 5, 2017 and is 27,376 bytes in size. The Sequence Listing contained in this .txt file is part of the specification and is hereby incorporated by reference herein in its entirety.

INTRODUCTION

Cancer vaccines target antigens expressed by tumors, but application of these vaccines has not been as effective as once hoped due to induction of immune tolerance by chronic overexpression of the targeted protein in the absence of co-stimulatory molecules and the induction of an immunomodulatory environment. Preventative cancer vaccines may be more promising, but cancers are highly variable, with multiple genetic changes, but few truly universal changes. Thus, it is difficult to predict what antigens will be overexpressed on any specific cancer or whether an individual should be vaccinated and if so, with what antigens and using what vaccination strategies. Accordingly, there remains a need in the art to identify cancer-specific antigens that may be used in cancer vaccines.

SUMMARY

Provided herein are compositions and methods for preventing and treating cancer. More specifically, the present invention relates to antigenic polypeptides and their use in cancer vaccines that may be used, in part, to treat cancer types dependent upon HER2-mediated signaling.

In one aspect, HER3 antigenic polypeptides are provided. The HER3 antigenic polypeptide may include a polypeptide having at least 50%, 55%, 60%, 65%, 70%, 75%, 80%, 85%, 90%, 95%, 98%, or 99% sequence identity to SEQ ID NO: 1 (LAEVPDLLE), SEQ ID NO: 2 (YMVMVKCW-MIDENI), SEQ ID NO: 3, SEQ ID NO: 8 or a fragment consisting of at least 5, 6, 7, 8, 9, or more amino acids of one of SEQ ID NO: 1, 2, 3 or 8 or a polypeptide having at least 50%, 55%, 60%, 65%, 70%, 75%, 80%, 85%, 90%, 95%, 98%, or 99% sequence identity to at least one of SEQ ID NO: 9, 10 or 11.

In another aspect, vectors are provided. The vectors may include a promoter operably connected to a first polynucleotide encoding any one of the HER3 antigenic polypeptides described herein.

In a further aspect, vaccine compositions including any of the HER3 antigenic polypeptide or polynucleotide compositions described herein are also provided. The vaccine compositions may include a pharmaceutical carrier, excipient, diluent or adjuvant.

In yet another aspect, methods of treating a cancer or precancer, or of reducing the likelihood of the cancer or precancer developing resistance to a cancer therapeutic or prevention agent in a subject are also provided. The methods include administering a therapeutically effective amount of any one of the HER3 antigenic compositions described herein to the subject having the cancer or precancer.

BRIEF DESCRIPTION OF THE DRAWINGS

FIG. 1 is a bar graph showing data from Interferon gamma (IFN-γ) enzyme-linked immunospot (ELISPOT) assays using the HER3$_{917-925}$ (SEQ ID NO: 1) and HER3$_{943-954}$ (SEQ ID NO: 3) peptides.

DETAILED DESCRIPTION

Figure 2A:
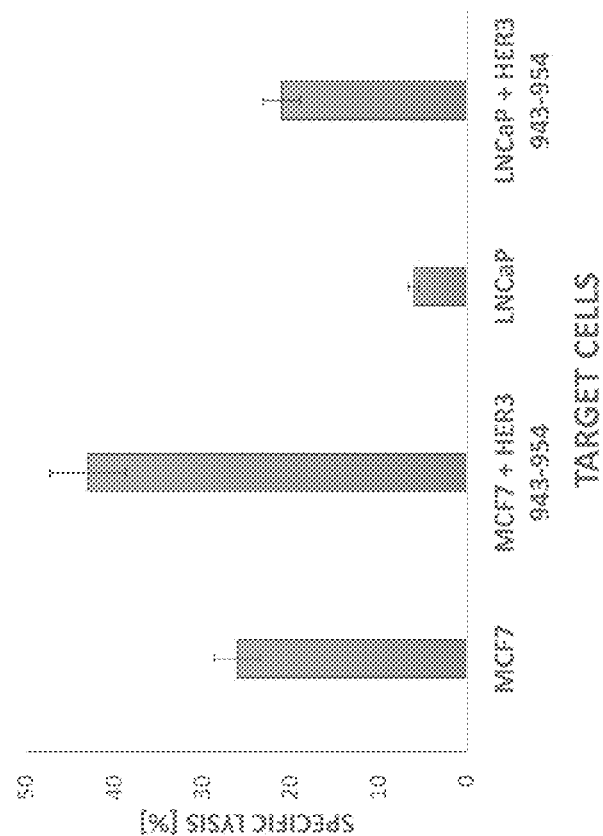
FIG. 2A is a bar graph showing data from human cytotoxic T cell (CTL) assays using the HER3$_{917-925}$ (SEQ ID NO: 1) peptide.

This application generally relates to antigenic HER3 polypeptides and their use in cancer vaccines that may be used, in part, to treat cancer types dependent upon HER2-mediated signaling cancer vaccines. The antigenic polypeptides were identified as T-cell antigens that are expressed in response to resistance to therapeutic intervention to cancer (or pre-cancers). Methods of using the vaccines to treat cancer are also provided.

HER3 is well known to mediate resistance to multiple therapies in breast cancer as well as plays a role in the development of breast and other cancers. To immunologically target this cancer, it is imperative to understand which epitopes might be presented on the cellular surface that would be targetable by antigen-specific T-cells. This knowledge will enable more effective vaccines to stimulate these types of T-cells through a variety of different vaccine platforms and enable the induction of effective immune responses that will selectively target cells that present HER3 epitopes. In the Examples, to identify such peptides, the present inventors have engineered cell lines overexpressing HER3 and utilized HLA pull down approaches combined with peptide stripping and mass spectrometry to identify HER3 presented polypeptides that would be attractive vaccine targets.

This invention would optimally be utilized through the inclusion of these antigenic HER3 polypeptides in different immune stimulatory vector systems, which would encompass but not be limited to various viral vectors (adenoviral, fowlpox, vaccinia, VEE, etc.), DNA-based vaccination vectors, and protein/peptide vaccination strategies. These antigenic HER3 polypeptides could be used prior to the development of cancer types dependent upon HER2-mediated signaling, used in front line or adjuvant settings as a treatment for these cancer, and also as a preventative measure to prohibit the development and evolution of this signaling pathway as a resistance pathway.

HER3 antigenic polypeptides are provided. The HER3 antigenic polypeptide may include a polypeptide having at least 50%, 55%, 60%, 65%, 70%, 75%, 80%, 85%, 90%, 95%, 98%, or 99% sequence identity to SEQ ID NO: 1

(LAEVPDLLE), SEQ ID NO: 2 (YMVMVKCWMIDENI), or a fragment consisting of at least 5, 6, 7, 8, 9, or more amino acids thereof. In some embodiments, the HER3 antigenic polypeptide may consist of a polypeptide having at least 50%, 55%, 60%, 65%, 70%, 75%, 80%, 85%, 90%, 95%, 98%, or 99% sequence identity to SEQ ID NO: 1 (LAEVPDLLE), SEQ ID NO: 2 (YMVMVKCWMIDENI), or SEQ ID NO: 3 (VMVKCWMIDENI).

As used herein, the terms "protein" or "polypeptide" or "peptide" may be used interchangeably to refer to a polymer of amino acids. A "polypeptide" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The HER3 antigenic polypeptides disclosed herein may include "mutant" HER3 antigenic polypeptides and variants, mutants, and derivatives thereof. As used herein the term "wild-type" is a term of the art understood by skilled persons and means the typical form of an organism, strain, gene or characteristic as it occurs in nature as distinguished from mutant or variant forms. As used herein, a "variant, "mutant," or "derivative" refers to a polypeptide molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a HER3 antigenic mutant or variant molecule may have one or more insertions, deletions, or substitution of at least one amino acid residue relative to the HER3 antigenic "wild-type" polypeptide sequence of a particular organism. The polypeptide sequences of the "wild-type" HER3 antigenic polypeptides from humans are presented as SEQ ID NOS: 1-3 and 8. The full length HER3 polypeptide is presented as SEQ ID NO: 9. These sequences may be used as reference sequences.

The HER3 antigenic polypeptides provided herein may be full-length polypeptides (as in SEQ ID NOs: 1-3 and 8) or may be fragments of the full-length polypeptide (e.g., SEQ ID NO: 3 is a fragment of SEQ ID NO: 2). The HER3 antigenic polypeptides may be encompassed in a fragment of full-length HER3. For example, the antigenic polypeptides are all within the intracellular domain of HER3 which is presented as SEQ ID NO: 10 and includes amino acids 666-1242 of the full-length HER3 or may include only a portion of the intracellular domain encompassing amino acids 741-954 of the full-length polypeptide as shown in SEQ ID NO: 11. As used herein, a "fragment" is a portion of an amino acid sequence which is identical in sequence to but shorter in length than a reference sequence. A fragment may comprise or consist of up to the entire length of the reference sequence (e.g., SEQ ID NOs: 1-3 or 8), minus at least one amino acid residue. In some embodiments, a fragment of the HER3 antigenic polypeptides may comprise or consist of at least 5, 6, 7, 8, 9, or more amino acids thereof. Preferably, a fragment of a HER3 antigenic polypeptide includes the amino acid residues responsible for eliciting an immune response such as a T cell response in a subject.

A "deletion" in a polypeptide refers to a change in the amino acid sequence that results in the absence of one or more amino acid residues. A deletion may remove at least 1, 2, 3, 4, 5, 6 or more amino acids residues. A deletion may include an internal deletion and/or a terminal deletion (e.g., an N-terminal truncation, a C-terminal truncation or both of a reference polypeptide).

"Insertions" and "additions" in a polypeptide refer to changes in an amino acid sequence resulting in the addition of one or more amino acid residues. An insertion or addition may refer to 1, 2, 3, 4, 5, 6 or more amino acid residues. A variant of a HER3 antigenic polypeptide may have N-terminal insertions, C-terminal insertions, internal insertions, or any combination of N-terminal insertions, C-terminal insertions, and internal insertions.

Regarding polypeptides, the phrases "% sequence identity," "percent identity," and "% identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent sequence identity for amino acid sequences may be determined as understood in the art. (See, e.g., U.S. Pat. No. 7,396,664).

The amino acid sequences of the HER3 antigenic polypeptide variants, mutants, or derivatives as contemplated herein may include conservative amino acid substitutions relative to a reference amino acid sequence (e.g., SEQ ID NOS: 1-3 or 8). For example, a variant, mutant, or derivative HER3 antigenic polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

It will also be appreciated by those of skill in the art that the "wild-type" HER3 antigenic polypeptide sequences from different organisms may be aligned to determine amino acid positions within the protein that may altered in order to create variant or mutant forms of the protein that may be expected to retain the immunogenicity of the HER3 antigenic polypeptide.

Vectors are also provided. The vectors may include a promoter operably connected to a first polynucleotide encoding any one of the HER3 antigenic polypeptides described herein. The vectors may include an origin of replication suitable to allow maintenance of the polynucleotide within a prokaryotic or eukaryotic host cell or within a viral nucleic acid. The vector may be viral vectors including, without limitation, an adenovirus, adeno-associated virus, fowlpox, vaccinia, viral equine encephalitis virus, or venezuelan equine encephalitis virus. In some embodiments, the vector is a DNA-based plasmid vector.

The vector may also be mini-circle DNA (mcDNA) vectors. Mini-circle DNA vectors are episomal DNA vectors that are produced as circular expression cassettes devoid of any bacterial plasmid DNA backbone. See, e.g. System Biosciences, Mountain View Calif., MN501A-1. Their smaller molecular size enables more efficient transfections and offers sustained expression over a period of weeks as compared to standard plasmid vectors that only work for a few days. The minicircle constructs can be derived from a plasmid with a bacterial origin of replication and optionally antibiotic resistance genes flanked by att sites to allow for recombination and exclusion of the DNA between the att sites and formation of the minicircle DNA.

As used herein, a "heterologous promoter" refers to any promoter not naturally associated with a polynucleotide to which it is operably connected. Promoters useful in the practice of the present invention include, without limitation, constitutive, inducible, temporally-regulated, developmentally regulated, chemically regulated, physically regulated (e.g., light regulated or temperature-regulated), tissue-preferred, and tissue-specific promoters. Promoters may include pol I, pol II, or pol III promoters. In mammalian cells, typical promoters include, without limitation, promoters for Rous sarcoma virus (RSV), human immunodeficiency virus (HIV-1), cytomegalovirus (CMV), SV40 virus, and the like as well as the translational elongation factor EF-1α promoter or ubiquitin promoter. Those of skill in the art are familiar with a wide variety of additional promoters for use in various cell types.

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Suitably the polynucleotide encodes the full-length HER3 antigenic polypeptide, however, polynucleotides encoding partial, fragment, mutant, variant, or derivative HER3 antigenic polypeptide are also provided. In some embodiments, the polynucleotides may be codon-optimized for expression in a particular cell.

The first polynucleotide encoding any of the HER3 antigenic polypeptides described herein may also be fused in frame to a second polynucleotide encoding fusion partners such as fusion polynucleotides or polypeptides which provide additional functionality to the antigenic cargo. For example, the second polynucleotide may encode a polypeptide that would target the HER3 antigenic polypeptide to the exosome, or would enhance presentation of the HER3 antigenic polypeptide, or would stimulate immune responses to the HER3 antigenic polypeptide. In some embodiments, the polynucleotide constructs described herein include a first polynucleotide encoding any of the HER3 antigenic polypeptides described herein that is fused in frame to a second polynucleotide encoding a lactadherin polypeptide or portions thereof. Lactadherin is a protein that is trafficked to exosomes though its C1C2 domain, a lipid binding domain. The lactadherin polypeptide may include SEQ ID NO: 4 (C1C2 domains of mouse lactadherin) or a homolog thereof.

In another embodiment, the polynucleotide constructs or the encoded HER3 antigenic polypeptides may be fused with polynucleotides or their encoded polypeptides that allow delivery to and/or fusion with a cell. For example, fusion with a Herpes Simplex Virus VP16 may allow for the cellular delivery of the HER3 antigenic polypeptide. Other potential fusion protein partners are ligands for receptors found on the target cells such that the peptides will be taken up by the cells via receptor-mediated endocytosis.

The HER3 antigenic polypeptides described herein may also be altered to make them more stable for delivery. Polypeptides may also be circularized or dimerized using any other means known to those of skill in the art. Addition of a methionine to the N-terminus of the HER3 antigenic polypeptides provided herein can be used as a target to generate a circularized peptide using the method of Tam and Xu (Biopolymers (1998) Methionine ligation strategy in the biomimetic synthesis of parathyroid hormones 46: 319-329). The polypeptides may have substituents bonded to either terminus of the peptide. For example, the peptide may have an acetyl or a carbamyl addition at the N-terminus, and/or an amide addition at the C-terminus. Those of skill in the art will appreciate that various additional modifications of the polypeptides provided herein may be made to increase the stability or half-life of the peptides in culture or in the subject after administration. For example fatty acids or other modifications may be added to the N-terminus including but not limited to formylation, myristoylation, or PEGylation. The HER3 antigenic polypeptide may be attached to a carrier protein to increase the stability of the peptide. The carrier protein-peptide may be a fusion protein and may be expressed as a recombinant protein using techniques available to those of skill in the art. The peptide bonds connecting the amino acids of the polypeptide may be altered or at least one peptide bond may be altered to make the peptides more resistant to degradation, for example a methyl group could be added. The amino acids could be replaced with functionally related non-natural amino acid that share similar side chains to the natural amino acid, such as replacement of the cysteine with homocysteine or α-methyl-cysteine.

Vaccine compositions including any of the HER3 antigenic polypeptide or polynucleotide compositions described herein are also provided. The vaccine compositions may include a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

The vaccine compositions described herein may include adjuvants to increase immunogenicity of the composition. In some embodiments, these compositions comprise one or more of a mineral adjuvant, gel-based adjuvant, tensoactive agent, bacterial product, oil emulsion, particulated adjuvant, fusion protein, and lipopeptide. Mineral salt adjuvants include aluminum adjuvants, salts of calcium (e.g. calcium phosphate), iron and zirconium. Gel-based adjuvants include aluminum gel-based adjuvants and acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gram-negative bacteria (e.g. from *Mycobacterium* spp., Corynebacterium parvum, C. granulosum, Bordetella pertussis and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate (TDM), cholera toxin or other bacterial toxins, and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein. Notably, several of the delivery particles noted above may also act as adjuvants.

In some embodiments, the vaccine compositions further include cytokines (e.g. IFN-γ, granulocyte-macrophage colony stimulating factor (GM-CSF) IL-2, or IL-12) or immunostimulatory molecules such as FasL, CD40 ligand or a toll-like receptor agonist, or carbohydrate adjuvants (e.g. inulin-derived adjuvants, such as, gamma inulin, algammulin, and polysaccharides based on glucose and mannose, such as glucans, dextrans, lentinans, glucomannans and galactomannans). In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). Modulation of the Immune Response to Vaccine Antigens. Dev. Biol. Stand, Vol. 92. Basel: Karger 1998; 19-28 and/or Sayers et al. J Biomed Biotechnol. 2012; 2012: 831486, and/or Petrovsky and Aguilar, Immunology and Cell Biology (2004) 82, 488-496.

In some embodiments, the adjuvant is an aluminum gel or salt, such as aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

In some embodiments, pharmaceutical compositions include oil-in-water emulsion formulations, saponin adjuvants, ovalbumin, Freunds Adjuvant, cytokines, and/or chitosans. Illustrative compositions comprise one or more of the following:

(1) ovalbumin (e.g. ENDOFIT);

(2) oil-in-water emulsion formulations, with or without other specific immunostimulating agents, such as: (a) MF59 (PCT Publ. No. WO 90/14837), which may contain 5% Squalene, 0.5% Tween 80, and 0.5% Span 85 (optionally containing various amounts of MTP-PE) formulated into submicron particles, (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, Mo.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+ CWS (DETOX™); and (d) ADDAVAX (Invitrogen);

(3) saponin adjuvants, such as STIMULON (Cambridge Bioscience, Worcester, Mass.);

(4) Complete Freunds Adjuvant (CFA) and Incomplete Freunds Adjuvant (IFA);

(5) cytokines, such as interleukins (by way of non-limiting example, IL-1, IL-2, IL-4, IL-5, IL-6, IL-7, IL-12, etc.), interferons (e.g., gamma interferon), macrophage colony stimulating factor (M-CSF), tumor necrosis factor (TNF), etc;

(6) chitosans and other derivatives of chitin or poly-N-acetyl-D-glucosamine in which the greater proportion of the N-acetyl groups have been removed through hydrolysis; and (7) other substances that act as immunostimulating agents to enhance the effectiveness of the composition, e.g., monophosphoryl lipid A.

In other embodiments, adjuvants include a flagellin-based agent, an aluminium salt or gel, a pattern recognition receptors (PRR) agonist, CpG ODNs and imidazoquinolines. In some embodiments, adjuvants include a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent.

Suitably, the vaccines described herein are capable of eliciting an immune response to a HER3 polypeptide when administered to a subject. Preferably, the immune response comprises a T cell mediated response.

Methods of treating a cancer or precancer, or of reducing the likelihood of the cancer or precancer developing resistance to a cancer therapeutic or prevention agent in a subject are also provided. The methods include administering a therapeutically effective amount of any one of the HER3 antigenic compositions described herein to the subject having the cancer or precancer. The subject may be any mammal, suitably a human, domesticated animal such as a dog or cat, or a mouse or rat. In some embodiments, the cancer therapeutic or prevention agent may be administered concurrently with, before or after administration of the HER3 antigenic composition.

Exemplary cancers in accordance with the present invention include, without limitation, primary and metastatic breast, ovarian, liver, pancreatic, prostate, bladder, lung, osteosarcoma, pancreatic, gastric, esophageal, colon, skin cancers (basal and squamous carcinoma; melanoma), testicular, colorectal, urothelial, renal cell, hepatocellular, leukemia, lymphoma, multiple myeloma, head and neck, and central nervous system cancers or pre-cancers. In some embodiments, the cancer may be HER2 positive. The cancer may be selected from any cancer capable of developing resistance to a therapeutic agent by increasing expression or activation of a protein by the cancer cells. In particular the cancer may be any cancer capable of developing resistance to a therapeutic agent which targets a HER family tyrosine kinase, suitably HER2 or EGFR or the estrogen receptor, suitably anti-estrogens. The cancer may develop resistance by increasing the expression of HER3, which although not a kinase, will dimerize with another HER family kinase and allow for signaling to occur.

Treating cancer includes, without limitation, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

A "therapeutically effective amount" or an "effective amount" as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The cancer therapeutic or prevention agents may be any agent capable of treating the cancer or inhibiting growth of cancer cells. Suitable agents include those which target HER2, HER1/EGFR, estrogen receptor or IGF1R. The therapeutic agent may be trastuzumab, lapatinib, pertuzumab or another HER2 targeting therapeutic agent or it may be an EGFR targeting therapeutic agent such as cetuximab or erlotanib, or it may be an antiestrogen, or an agent that prevents estrogen synthesis such as an aromatase inhibitor.

Suitably the vaccinated subject develops an immune response to HER3 in response to administration of the vaccine. The immune response may be an antibody or T cell immune response. For example the immune response may include antibody-dependent cellular cytotoxicity, polyclonal antibody response, complement dependent cellular cytotoxicity, cellular cytotoxicity, disruption of ligand binding, disruption of dimerization, mimicking ligand binding causing internalization of HER3, or degradation of HER3. The immune response may comprise an antibody response directed to at least one of SEQ ID NOs: 1-3 or 8.

Reduction of the development of resistance can be measured in several ways. The resistance of the vaccinated subject may be compared to a similar subject that was not vaccinated. Alternatively, the reduction may be measured based on statistics generated regarding the likelihood of an individual being treated with the therapeutic agent to develop resistance versus that of individuals treated with the therapeutic agent and vaccinated with HER3. The reduction in the likelihood of resistance of the cancer may also be measured by measuring the level of HER3 expression on the surface of cancer cells. HER3 expression is reduced on cancer cells after effective administration of the vaccine. The effectiveness of the vaccine in treating the cancer or reducing the likelihood of resistance can be measured by tracking the growth of the tumor or the growth rate of the tumor or cancer cells. A decrease in tumor size or in the rate of tumor growth is indicative of treatment of the cancer.

Co-administration, or administration of more than one composition (i.e. the HER3 antigenic compositions and cancer therapeutic or prevention agents) to a subject, indicates that the compositions may be administered in any order, at the same time or as part of a unitary composition. The two compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

The compositions (i.e. the HER3 antigenic compositions and cancer therapeutic or prevention agents) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal absorption. Thus the compositions may be formulated as an ingestable, injectable, topical or suppository formulation. The compositions may also be delivered with in a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compositions will reduce the growth of the cancer at least 10%, 20%, 30%, 40%, 50%, 60%, 70%, 80%, 90%, 100% or more as compared to no treatment or treatment with only the therapeutic agent. It is specifically contemplated that vaccine preparations and compositions may palliate, block further growth or alleviate symptoms associated with the cancer without providing a cure, or, in some embodiments, may be used to cure the cancer and rid the subject of the disease.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The HER3 antigenic compositions described herein may be administered one time or more than one time to the subject to effectively boost the immune response against HER3. If the vaccine is provided as a vector, the vector may be administered based on the number of particles delivered to the subject (i.e. plaque forming units or colony forming units). The subject may be administered $10^{12}$, $10^{11}$, $10^{10}$, $10^9$, $10^8$, $10^7$ or $10^6$ particles.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1

Identification of HER3 Peptides Presented by MHC Proteins

Discovery of HER-3-Derived Peptides $10^9$ cultured breast cancer cells (MCF-7) were washed with PBS (phosphate-buffered saline) to remove serum proteins and resuspended in lysis buffer (1% NP40, 150 mM NaCl, 10 mM $Na_2HPO_4$, 1 mM EDTA, protease inhibitors, Sigma-Aldrich). Cell suspensions were frozen and thawed 3 times to facilitate efficient lysis. After removing cellular debris, cell lysates were subjected to two rounds of immunoprecipitation using 1 mg pan HLA class I-specific antibody and 1 mL of Protein A/G beads (Pierce Biotechnology). The sample solution containing isolated MHC/peptides complexes was heated at 85° C. (15 min), to further dissociate any bound peptide from heavy chains. After cooling to room temperature, peptides were separated from the antibody and HLA molecules by size-exclusion centrifugation (Amicon Ultra-3 10 kDa molecular mass cutoff membrane filters, Millipore). The filtrate was concentrated using vacuum centrifugation and subjected to HPLC (high performance liquid chromatography) and MS (mass spectrometry) analyses. Lastly, synthetic peptides were synthesized for the MHC class I-bound peptides that were identified by HPLC-MS analyses, and the sequences was confirmed under identical conditions of collision used to identify the MHC class I bound peptides.

Using the methods described above, we identified four HER3 peptides that were presented by MHC proteins: $HER3_{917-925}$ (LAEVPDLLE (SEQ ID NO: 1)), $HER3_{941-954}$ (YMVMVKCWMIDENI (SEQ ID NO: 2)), $HER3_{943-954}$ SEQ ID NO: 3 (VMVKCWMIDENI (SEQ ID NO: 3)) and $HER3_{741-749}$ (IKVIEDKSG (SEQ ID NO: 8)).

See Table 1. The number provided in subscript refers to the amino-acid position of our epitopes within the full-length human HER3 protein (Genebank sequence ID AAA35979.1 (SEQ ID NO: 9)).

TABLE 1

HER3-derived peptide epitopes

| | |
|---|---|
| $HER3_{917-925}$ | LAEVPDLLE (SEQ ID NO: 1) |
| $HER3_{941-954}$ | YMVMVKCWMIDENI (SEQ ID NO: 2) |
| $HER3_{943-954}$ | VMVKCWMIDENI (SEQ ID NO: 3) |
| $HER3_{741-749}$ | IKVIEDKSG (SEQ ID NO: 8) |

Example 2

Testing the $HER3_{917-925}$ (SEQ ID NO: 1) and $HER3_{943-954}$ (SEQ ID NO: 3) Peptides in Immunological Assays Peptide Synthesis Peptides were synthesized by ChinaPeptides Co, Ltd (Beijing, China) using standard Fmoc (Fluorenylmethyloxycarbonyl)-based solid phase synthesis. The purity of peptides was >95%.

Peptide Vaccination of HLA-A*0201-Transgenic Mice

To further validate the identified HER-3-derived peptide epitopes (SEQ ID NO: 1 and SEQ ID NO: 3), we vaccinated HLA-A*0201-transgenic mice with these peptides. Female CB6F1-Tg(HLA-A*0201/H2-K$^b$) A*0201 mice were purchased from Charles River Laboratories (Raleigh, N.C.). These animals carry a transgene consisting of fragments of the human HLA-A*0201 gene and mouse H2-K$^b$ gene which encodes a chimeric class I molecule consisting of the human HLA-A2.1 leader, α1 and α2 domains ligated to the murine α3, transmembrane and cytoplasmic H2-K$^b$ domain Mice were maintained in a specific pathogen-free environment. All mice were used at 8 to 12 weeks of age. Animals were housed in a specific pathogen-free environment at the animal facility of the DUKE University Medical Center. All mice used in this study were cared for in accordance with the Guide for Humane care and use of Laboratory Animals published by the National Institutes of Health. All the animal experimental protocols were approved by the Duke University Medical Center Institutional Animal Care and Use Committee.

Mice were immunized with a mixture of 100 μg of each peptide emulsified in PBS:Montanide ISA 51 (1:1) (SEPPIC, France). Mice received 3 vaccinations at weekly intervals. For the first 2 vaccination, 200 μL peptide-Montanide emulsion was administered subcutaneously and the final vaccination (40 μL) was administered intradermally. Mice were sacrificed 10 days after the final vaccination and spleens were harvested for immunologic assays.

Interferon Gamma (IFN-γ) Enzyme-Linked Immunospot (ELISPOT) Assays

ELISPOT assays were performed without re-stimulation of cells. Untouched CD8$^+$ T cells (isolated via magnetic bead-based techniques (Miltenyi Biotec)) were used as responder cells in ELISPOT assays. After blocking wells with RPM medium supplemented with 20% FCS, $10^5$ cells murine CD8$^+$ T cells in 100 μl complete RPMI medium were added to each well of flat-bottomed 96-well nitrocellulose plates (MultiScreen-IP; Millipore Corp., Bedford, Mass., USA) pre-coated with 10 μg/ml of murine IFN-γ capture Ab (Mabtech USA), respectively. Plates were incubated for 24 hours at 37° C., and after washing, biotinylated IFN-γ detection Ab (1 μg/ml; Mabtech USA) was added to each well. Cells were incubated for an additional 2 hours at room temperature, then incubated with streptavidin-alkaline phosphatase (1 μg/ml, Sigma Chemical Co.) and developed with BCIP/NBT (5-Bromo-4-chloro-3'-indolyphosphate/Nitroblue tetrazolium chloride) substrate (Kirkegaard & Perry Laboratories, Gaithersburg, Md., USA). Spots of the dried plate were counted using an ImmunoScan ELISPOT reader (C.T.L., Cellular Technology Ltd.).

As shown in FIG. 1, IFN-γ ELISPOT reveals that only peptide $HER3_{943-954}$ (SEQ ID NO: 3) induced epitope-specific CD8$^+$ T cells in HLA-A*0201-transgenic cells that produced IFN-γ when stimulated with epitope $HER3_{943-954}$ (SEQ ID NO: 3)-pulsed T2 cells, while epitope $HER3_{917-925}$ (SEQ ID NO: 1) failed to induce CD8$^+$ T cells that produced IFN-γ upon stimulation with $HER_{917-925}$ (SEQ ID NO: 1) loaded T2 cells.

Generation of Human CTL (Cytotoxic T Cells)

Immature human DCs (Dendritic cells) were loaded for 2 hours at 10 μM with peptides, washed and then co-cultured with untouched autologous T cells (isolated via magnetic bead-based separation) at a DC to T-cell ratio of 1:20 in complete RPMI media supplemented with 12.5 μg/mL pIC, (polyinosinic-polycytidylic acid, Sigma) and 1.0 μg/mL recombinant CD40L plus 1.0 μg/mL Enhancer (Alexis Biochemicals). 20 U/ml of recombinant human Interleukin-2 (IL-2) were added after 3 days and every other day thereafter. Cells were re-stimulated twice after 7 days (DC to T cell ratio of 1:10) and analyzed for cytolytic activity 10 days after the last re-stimulation.

CTL Assays $2 \times 10^6$ target cells were harvested, washed, counted, and labeled with 100 μCi of $Na_2{}^{51}CrO_4$ (Amersham) in 0.5 ml complete RPMI at 37° C. for 1.5 h. Exogenous loading of cells with 10 μM synthetic peptide was performed simultaneously with labeling reactions. CTLs (untouched CD8$^+$ T cells isolated via magnetic-bead-based techniques (Miltenyi Biotec)) were washed, counted, and diluted to the desired density in complete RPMI 1640 and plated in duplicate wells in a round-bottomed, 96-well plate. Target cells were washed three times, resuspended in complete RPMI and incubated at 37° C. and 5% $CO_2$. After 1 h, cells were washed one more time, diluted to $10^4$ cells/ml and co-incubated with CTLs at indicated effector to target ratio of 25 to 1. The plates were spun briefly at 800×g and incubated for 4-5 h at 37° C. Supernatants were harvested and counted in a gamma counter. Duplicate wells were averaged, and the percentage of specific lysis was calculated as:

$$\% \text{ specific lysis} = \frac{\text{Experimental release} - \text{spontaneous release}}{\text{Maximum release} - \text{spontaneous release}} \times 100$$

Figure 2B:
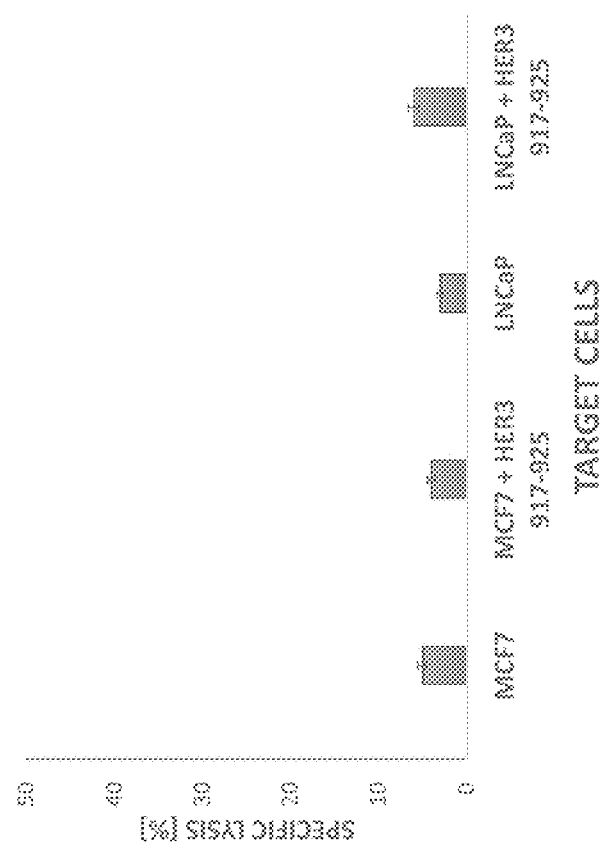
FIG. 2B is a bar graph showing data from human cytotoxic T cell (CTL) assays using the HER3$_{943-954}$ (SEQ ID NO: 3) peptide.

As shown in FIGS. 2A-2B, and in agreement with our animal data, peptide epitope $HER3_{917-925}$ (SEQ ID NO: 1) failed to induce HERS-specific CTLs, as evidenced by a lack of these cells to kill HLA-A*0201-positive- and HER3-positive MCF-7 cells (FIG. 2A). In contrast, $HER3_{943-954}$ (SEQ ID NO: 3)-induced CTL killed MCF-7 cells efficiently and the cytolytic activity could further be enhanced by loading of target cells with epitope $HER3_{943-954}$ (SEQ ID NO: 3). Expectedly, $HER3_{943-954}$ (SEQ ID NO: 3)-specific CTL did not kill HLA-A*0201-positive, but HER3-negative LNCaP cells (FIG. 2B). Killing of $HER3_{943-954}$ (SEQ ID NO: 3)-loaded LNCaP cells proves that these cells indeed express functional HLA-A*0201 molecules on their cell surface.

We claim:

1. A vector comprising a promoter operably connected to a first polynucleotide encoding a HER3 antigenic polypeptide consisting of the polypeptide of SEQ ID NO:2, SEQ ID NO:3 or a polypeptide having at least 90% sequence identity to SEQ ID NO: 2 or SEQ ID NO: 3.

2. The vector of claim 1, wherein the HER3 antigenic polypeptide consists of a polypeptide having at least 90% sequence identity to SEQ ID NO: 3.

3. The vector of claim 1, wherein the first polynucleotide is fused in frame to a second polynucleotide encoding a lactadherin polypeptide or portions thereof.

4. The vector of claim 3, wherein the lactadherin polypeptide comprises any one of SEQ ID NOS: 4-7 or a homolog thereof.

5. The vector of claim 1, wherein the vector is selected from the group consisting of an adenoviral vector, a fowlpox vector, a vaccinia vector, a VEE vector, a mini-circle DNA (mcDNA) vector, and a DNA-based vaccination vector.

6. A vaccine composition comprising the vector of claim 1 and a pharmaceutically-acceptable carrier.

7. The vaccine composition of claim 6, wherein the vaccine is capable of eliciting an immune response to a HER3 polypeptide when administered to a subject.

8. The vaccine composition of claim 7, wherein the immune response comprises a T cell mediated response.

9. A method of treating a cancer or precancerous cells or of reducing the likelihood of the cancer developing resistance to a cancer therapeutic or prevention agent in a subject comprising administering a therapeutically effective amount of the vector of claim 1 to the subject having the cancer or precancerous cells.

10. The method of claim 9, wherein the cancer is HER2 positive.

11. The method of claim 9, wherein the cancer or precancerous cells are selected from a breast, prostate, lung, ovarian, colon, rectal, pancreas, bladder, head and neck or liver cancer or precancerous cells.

12. The method of claim 9, wherein the subject develops an immune response to HER3.

13. The method of claim 12, wherein the immune response comprises a T cell mediated response.

14. The method of claim 9, wherein administration of the vector results in a reduction of HER3 expression on the cancer or precancerous cells after administration of the vector as compared to the level of HER3 on the cancer or precancerous cells prior to vaccination.

15. The method of claim 9, wherein administration of the vector results in decreased tumor growth rate or decreased tumor size after administration as compared to prior to administration.

16. The method of claim 9, further comprising administering a therapeutically effective amount of the cancer therapeutic or prevention agent to the subject.

17. The method of claim 16, wherein the vector is administered concurrently with, before or after administration of the cancer therapeutic or prevention agent.

18. The method of claim 16, wherein the cancer therapeutic or prevention agent is an agent targeting HER2, HER1, estrogen receptor, EGFR, or IGF1R.

19. The method of claim 16, wherein the cancer therapeutic or prevention agent is selected from the group consisting of trastuzumab, lapatinib, cetuximab, pertuzumab, and erlotanib.

* * * * *